United States Patent [19]
Lattes et al.

[11] Patent Number: 6,040,485
[45] Date of Patent: Mar. 21, 2000

[54] FLUORINATED ORGANIC COMPOUNDS, OPHTHALMOLOGICAL APPLICATIONS THEREOF AND METHOD FOR MAKING SAME

[75] Inventors: Isabelle Lattes, Ramonville Saint Agne; Bernard Feurer, Montlaur; Brigitte Guidetti, Flourens; Viviane Payrou, Toulouse, all of France

[73] Assignee: Chauvin Opsia, Castanet Tolosan, France

[21] Appl. No.: 09/029,486

[22] PCT Filed: Aug. 29, 1995

[86] PCT No.: PCT/FR95/01131

§ 371 Date: Feb. 26, 1998

§ 102(e) Date: Feb. 26, 1998

[87] PCT Pub. No.: WO97/08118

PCT Pub. Date: Mar. 6, 1997

[51] Int. Cl.$^7$ ..................... C07C 17/02
[52] U.S. Cl. ............... 570/126; 570/123; 570/124; 570/165; 570/166; 570/168; 570/169
[58] Field of Search ............... 570/123, 124, 570/126, 165, 166, 168, 169

[56] References Cited

PUBLICATIONS by C. Cecutti et al., "Potential Blood Substitutes Synthesis and Microemulsification of mixed Hydrogenated and Fluorinated Oils", *J. Dispersion Science and Technology*, vol. 7, No. 3, 1986, pp. 307–318.

by C. Cecutti et al., "New Formulation of Blood Substitutes; Optimization of Novel Fluorinated Microemulsions", *Eur. J. Med. Chem.*, vol. 24, 1989, pp. 485–492.

by C. Cecutti et al., "A New Formulation for Blood Substitutes", *J. Dispersion Science and Technology*, vol. 11, No. 2, 1990, pp. 115–123.

by A. Novelli, "Microemulsification et Biocompatibilite d'un Radioprotecteur Hydrophile et d'un Transporteur d'Oxygene Hydrophobe", *Le Titre De Docteur De L'Institut National Polytechnique De Toulouse*, May 1990, pp. 9–10; 13–31 and 217–218.

*Primary Examiner*—James O. Wilson
*Attorney, Agent, or Firm*—Young & Thompson

[57] ABSTRACT

The invention relates to novel fluorinated organic compounds having the following molecular structure:

$$R_F\text{---}CH_2\text{---}CH\text{=}C\text{---}R_{2H}$$
$$|$$
$$R_{1H}$$

where $R_F$ is a fluorinated carbon chain, $R_{1H}$ is hydrogen or a saturated hydrogenated carbon chain, $R_{2H}$ is hydrogen or a saturated hydrogenated carbon chain, $R_{1H}$ and $R_{2H}$ being not simultaneously hydrogen, the group $$C\text{---}R_{2H}$$
$$|$$
$$R_{1H}$$

comprising a principal chain and at least one linear or cyclic branch. These compounds may be prepared by reacting a phosphine with a halide under heating, and then hot reacting in a solvent the resulting phosphonium salt with a branched aldehyde or a ketone. These compounds have an excellent stability, a good biocompatibility and a high capacity to solubilize gases and particularly oxygen, such properties allowing their use in applications of the ophthalmological type or as an organ preservation medium.

16 Claims, No Drawings

FLUORINATED ORGANIC COMPOUNDS, OPHTHALMOLOGICAL APPLICATIONS THEREOF AND METHOD FOR MAKING SAME

DESCRIPTION

1. Technical Field of the Invention

The present invention relates to novel fluorinated organic compounds having a fluorinated chain and a hydrogenated chain; the invention aims at applications of these novel compounds, particularly ophthalmological applications or as cell preservation medium, and relates to the method of making said compounds.

2. Background Art

Fluorinated compounds are known to have specific properties such as good stability, biocompatibility, and capacity to solubilize gases and specially oxygen, these properties being decisive in numerous applications.

Amoung these fluorinated compounds, specific compounds having a hydrogenated chain with a double bond: $R_F$—$CH_2$—$CH$=$CH$—$R_H$ where $R_F$ is a fluorinated carbon chain and $R_H$ a saturated hydrogenated linear chain were recently prepared. Reference may be made to the following publications relating to this type of linear compounds and the applications thereof as blood substitutes or replacement of the vitrous humor in the eye: C. Cecutti et al., POTENTIAL BLOOD SUBSTITUTES SYNTHESIS AND MICROEMULSIFICATION OF MIXED HYDROGENATED AND FLUORINATED OILS, J. DISPERSION SCIENCE AND TECHNOLOGY, 7(3), 307–318 (1986); C. Cecutti et al., NEW FORMULTAION OF BLOOD SUBSTITUTES: OPTIMIZATION OF NOVEL FLUORINATED MICROEMULSIONS, Eur. J. Med. Chem. 24 (1989) 485–492 ; C. Cecutti et al., A NEW FORMULATION FOR BLOOD SUBSTITUTES, J. DISPERSION SCIENCE AND TECHNOLOGY, 11(2), 115–123 (1990). Anne NOVELLI, Thesis MICROEMULSIFICATION ET BIOCOMPATIBILITE D'UN RADIOPROTECTEUR HYDROPHILE ET D'UN TRANSPORTEUR D'OXYGENE HYDROPHOBE, I.N.P.T., presentation of May 18, 1990.

This family of linear fluorinated compounds has specific stability, density and oxygen solubilization properties which, in various applications, make the use thereof advantageous as compared to the other fluorinated compounds. Such properties result one the one hand from the central double bond and on the other hand from the hydrogenated chain located opposite to the fluorinated chain. The double bond reduces the volatility of the compound for a same number of carbons and increases their oxygen solubilization capacity. The presence of the hydrogenated chain leads to a density which is a function of the chain length, and which is lower than in the case of non hydrogenated fluorinated compounds having the same fluorinated chain. Accordingly, the combined choice of the fluorinated $R_F$ and hydrogenated $R_H$ chains allows to some extent to obtain liquid compounds with the desired density and number of fluorine atoms, i.e. a given oxygen solubilization capacity.

These linear fluorinated compounds are currently prepared by means of a method using the Wittig's reaction. However, the yield of this synthesis is low; for example, the average synthesis yields for fluorinated chains with eight carbon atoms are of the order of 50% (overall yield). Since the starting materials used in the Wittig's reaction are costly, the cost of the resulting linear fluorinated compounds is very high, which limits the possibility of their application considerably. To the knowledge of the inventors, these linear compounds were only synthesized in the laboratory for research purposes, and are not being used. Moreover, these linear compounds have good oxygen solubilization properties, provided that their fluorinated chain has a comparatively high number of carbon atoms, which is associated with high density compounds. For numerous applications, the density/oxygen solubilization compromise would therefore not be easy to obtain with such type of compounds.

DISCLOSURE OF THE INVENTION

The present invention aims at providing novel fluorinated organic compounds the properties thereof are at least as attractive as the above-mentioned linear fluorinated compounds, but with the benefit of higher synthesis yields, allowing a reduction in the preparation costs thereof in marked proportions, whereby the possibilities of application would be widened.

A further object of the invention is to provide fluorinated compounds having an increased oxygen solubilization capacity as compared to the above-mentioned linear compounds having the same fluorinated chain.

Yet a further object of the invention is to facilitate the adjustment of the physicochemical properties of the compound in each application, according to the specifications of the application.

In view of these objects, the novel compounds according to the invention have the following molecular structure:

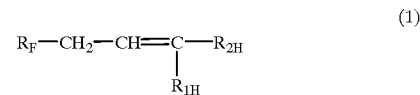
(1)

where $R_F$ is a fluorinated carbon chain, $R_{1H}$ is hydrogen or a saturated hydrogenated carbon chain, $R_{2H}$ is hydrogen or a saturated hydrogenated carbon chain, $R_{1H}$ and $R_{2H}$ being not simultaneously hydrogen, the group

comprising a principal chain and at least one linear or cyclic branch.

The organic compounds according to the invention are thus characterized by the following, in combination:
- the presence of a non reactive central double bond in the molecule,
- the presence, on the respective sides of the double bond of a fluorinated and a hydrogenated chain,
- the branched character of the hydrogenated chain.

These compounds are liquid at ambient temperature, perfectly biocompatible, the density, oxygen solubilization capacity and refractive index thereof varying as a function of the fluorinated and hydrogenated chains thereof. The oxygen solubilization capacity thereof appears to be markedly increased as compared to the similar (same fluorinated chain, similar total number of carbon atoms) linear compounds, and the preparation costs thereof are lower.

In a subfamily, the moiety $R_{1H}$ may be constituted of a hydrogen, the molecular structure of the compound being the following:

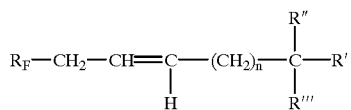
(2)

where the groups R', R" and R'", identical or not, have each the following formula: $(CH_2)_m-C_xH_y$, with:

$n \geq 0$ $m \geq 0$ $y=2x$ or $2x+1$ with $x \geq 0$ at least two of the groups R', R" and R'" are not hydrogen atoms, the total number of carbon atoms of the groups R', R" and R'" being lower than $25-n$.

The group $C_xH_y$ may particularly consist of one or more methyl, ethyl or propyl groups, so as to lead to compounds which, as will be more apparent hereinafter, have very advantageous properties in ophthalmological applications, particularly the three compounds with the following structure:

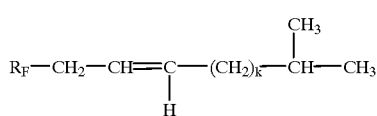
(3)

where k=1, 2, or 3.

The following compound in the above-mentioned subfamily has a high refractive index of approx. 1.37, which makes it very attractive in ophthalmological applications because of the difference between such index and that of physiological serum (1, 33), which facilitates the use thereof (improved injection and removal due to a perfect visualization of the product):

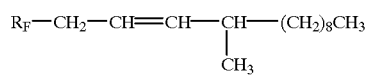
(4)

In a further subfamily, neither $R_{1H}$ and $R_{2H}$ moieties are hydrogen, the compounds having the following molecular structure:

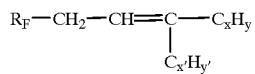
(5)

where $y=2x+1$, with $x \geq 1$, $y'=2x'+1$, with $x' \geq 1$.

In this subfamily, the groups $C_xH_y$ and $C_{x'}H_{y'}$ may also be methyl, ethyl or propyl groups.

The fluorinated chain $R_F$ may be a perfluorinated or non perfluorinated chain, and may possibly comprise a heteroatom. The presence of a perfluorinated chain with a formula $C_pF_{2p+1}$ with p in the range between 2 and 12 is preferred in various applications, due to its improved stability. The branched compounds having such chain have a density which is in the range between 1.1 and 2.2 and increases as a function of p (and which decreases to a lesser extent as a function of the number of carbon atoms in the branched hydrogenated chain). The refractive index of such branched compounds with a perfluorinated chain is comprised between 1.2 and 1.7, as a function of p and the number of carbon atoms in the $R_{1H}$ and $R_{2H}$ moieties. The solubility in silicone oil of such compounds is greater than 10 wt %.

The novel branched fluorinated compounds according to the invention may be prepared using a Wittig's reaction: it was unexpectedly observed that the overall synthesis yields are higher than with known linear compounds having the same fluorinated chain. This result currently remains hardly explained, but one may suppose it derives from a lower volatility of the branched compounds. For example, in a case where the $R_F$ chain consists of the perfluorinated chain with eight carbon atoms $C_8F_{17}$, the overall synthesis yield is about 70% (namely a relative increase of 40% as related to the synthesis yield of similar linear compounds); furthermore, an improved reproducibility of the results is observed, the synthesis of linear compounds depending tightly of the conditions under which the reaction is carried out. Moreover, it was evidenced that with an equivalent number of carbon atoms, the oxygen solubilization capacity is significantly higher for the branched compounds according to the invention (as compared to linear compounds with a same number of carbon atoms). This may be explained by the fact that, in the case of the compounds according to the invention, this oxygen solubilization capacity results not only from the fluorinated chain but also from the branched portions of the molecules, by a sterical hindrance effect.

DESCRIPTION OF A PREFERRED EMBODIMENT

In the general embodiment thereof, the method for preparing the branched fluorinated compounds according to the invention comprises the following steps:

a phosphine $Z_3P$ is reacted with a halogenide of the formula $XCH_2CH_2R_F$ in order to obtain a phosphonium salt $Z_3P^+X^-CH_2CH_2R_F$, and said phosphonium salt is reacted in a solvent with a branched aldehyde or ketone

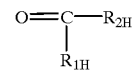

in the presence of a weak base.

For preparing a compound of the subfamily (2), the phosphonium salt is reacted under heating with a branched aldehyde of the following structure:

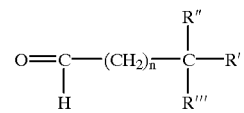

In the case of the three above-mentioned compounds (3), a triphenylphosphine $(C_6C_5)_3P$ may be selected as the phosphine and a fluoroalkyl iodide $I(CH_2)_2R_F$ as the halogenide. The resultant phosphonium salt is then reacted with the following branched aldehyde:

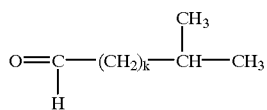

where k=1, 2, or 3. Dioxane is preferably used as a solvent, in the presence of potassium carbonate and water acting as a catalyst. The reaction temperature is then adjusted to the reflux temperature of the dioxane. The potassium carbonate may subsequently be removed by filtration, and the resultant triphenylphosphine oxide is removed by precipitation followed by filtration, the branched fluorinated compound being collected by means of distillation steps.

For preparing a compound of the subfamily (5), the phosphonium salt is reacted under heating with a ketone of the following formula:

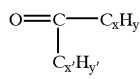

The branched fluorinated compounds according to the invention may be used for preparing an artificial composition of vitrous or aqueous humor for an eye, particularly compounds (2) where the group $C_xH_y$ consists of one or more of methyl, ethyl and/or ethyl groups.

The following compounds:

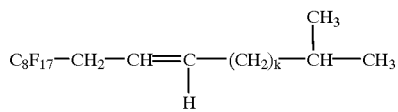

(7)

where k=1, 2, or 3, are particularly adapted for preparing an artificial composition for the temporary replacement of the vitrous humor in the eye with view of a re-adhesion of the retina. The density of such compounds is comprised in the range between 1.48 and 1.54 and the refractive index between 1.33 and 1.35.

In ophthalmological applications and more generally in applications where a high purity is prescribed, the synthesis method is complemented with the final purification steps of: combined extraction in organic and aqueous phases, adapted for removing the remaining traces of the solvent and phosphine oxide, removal of the aqueous phase by means of decantation, evaporation of the organic phase, flash distillation under vacuum and cooling of the resultant product with nitrogen, and subjecting the resultant product to filtration and neutralization steps in order to remove the last residues.

It was besides observed that the branched fluorinated compounds according to the invention have a good solubility in silicone and fluorosilicone oils. This property allows, when needed, their use in the form of a solution or suspension in this oil so that products having the properties of silicone or fluorosilicone oils and an adjustable density greater or equal to 1 are obtained. Oils having a viscosity in the range between 100 cSt and 10,000 cSt are advantageously used for this purpose. For example, in the field of ophthalmology, the above-mentioned compounds (2) or (7) may be used as a solution in a silicone or fluorosilicone oil, for the preparation of an artificial composition to replace the vitrous or aqueous humor in the eye in order to provide an internal buffer effect in the eye. This provides a further means for decreasing the density and adjusting same to the desired value, particularly for products intended to remain in the eye for long periods. Moreover, in some ophthalmological applications, this allows also to combine the properties of the silicone oils with the properties (viscosity, density, refractive index) of the compounds according to the invention. It should be noted that the high solubility of the compounds according to the invention in silicone oils avoids any risk of formation of an emulsion or interface in the mass.

The branched fluorinated compounds according to the invention may also be used in all applications where the oxygen solubilization capacity is desired, particularly for preparing a medium for the preservation of biological organs, tissues or cells, particularly a medium for the preservation of ocular tissues such as corneae.

The following examples are intended to illustrate the invention.

EXAMPLES

Example 1

Preparation of Compound

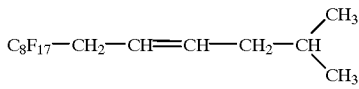

Step 1: Preparation of phosphonium salt 226 g of triphenylphosphine $(C_6H_5)_3P$ and 500 g of fluoroalkyl iodide I—$CH_2$—$CH_2$—$C_8F_{17}$ are placed in a 2-liter reactor.

Heating at 110° C. is carried out during 12 hours with stirring.

The final product sets into a mass. It is washed with toluene, then with ether and dried at 40° C. under vacuum ($10^3$ Pa) during 12 hours.

The yield of phosphonium salt of formula: $I^-(C_6H_5)_3P^+$—$CH_2$—$CH_2$—$C_8F_{17}$ is about 95 % (as determined by NMR and microanalysis).

Step 2: Wittig's reaction

The Wittig's reaction is conducted in phase transfer conditions.

512 g of the phosphonium salt obtained in preceding step, 42 g of isovaleraldehyde $(CH_3)_2$ CH—$CH_2$—CHO, 101 g of $K_2CO_3$, 6.6 g of water and 488 ml of dioxane are placed in a 2-liter reactor.

Water solvates the potassium K+ and releases the $CO_3^{2-}$ ion, resulting in mild basic conditions.

Heating is conducted at the reflux temperature of the dioxane (100° C.) during 18 hours with strong stirring. A brownish pasty mixture is obtained.

$K_2CO_3$ is removed by means of filtration while rinsing with dioxane.

Dioxane is evaporated under vacuum ($10^3$ Pa) and the triphosphine oxide is caused to precipitate by addition of cold ether (4° C.).

The precipitate is removed by filtration, and the ether is evaporated under vacuum ($10^3$ Pa) in cold conditions.

The product (amber liquid) is then subjected to a double extraction, both with water and hexane (1V/1V/1V). The last traces of the dioxane and triphenylphosphine are thus removed.

The organic phase is washed three times with water (1V/1V).

The hexane is evaporated under vacuum ($10^3$ Pa) in cold conditions. A flash distillation under vacuum of the type "bulb to bulb" is then carried out: the trap is cooled with liquid nitrogen; when the vacuum reaches 1 to 10 Pa, heating to 40° C. is conducted, the possible traces of solvents and water are removed in a first portion, and the synthesized hydrogenated fluorinated organic compound is collected by means of heating at approx. 100° C.

The resultant product is transparent.

It is once again washed with water and treated with active carbon before being filtered on a 0.22 μm-sized filter.

The reaction yield of the branched fluorinated compound is about 80%; accordingly, the global preparation yield is 76%.

It should be noted that this yield is approximately 50% higher in relative value than that obtained in the synthesis of the linear compound $C_8F_{17}$—$CH_2$—$CH$=$CH$—$CH_2$—$CH_2$—$CH_2$—$CH_3$.

A transparent liquid able to be packaged in flasks is obtained.

Example 2
Characterization of Compound

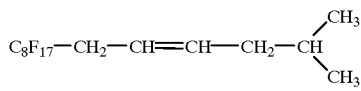

The hydrogenated fluorinated organic compound obtained by means of the above-described synthesis has the following physico-chemical properties (as measured by densitometry, refractometry, tensiometry, viscometry, . . . ).

Aspect: Transparent liquid
Molecular weight: 516
Refractive index: 1.338
Density: 1.5
Surface tension: 18 mN/m (at 37° C., as measured by means of an automatic tensiometer)
Viscosity: $<5.10^{-6}$ m$^2$/s (namely 5 cSt)
Boiling point: 110° C. (under a pressure of 1 Pa)
$O_2$ absorption:

NMR spectrum of $C_8F_{17}$—$CH_2$—$CH$=$CH$—$CH_2$—$CH$—$(CH_3)_2$

NMR ($^{13}$C, 50 MHz, CDCl$_3$) ppm: 135.86 (s, 1C, CH$_\gamma$C$_8$F$_{17}$); 122.65–111.20 (m, 8 C, C$_8$F$_{17}$); 116.1 (t, 1C, CH$_\beta$C$_8$F$_{17}$); 36.36 (s, 1C, CH$_2$ in β double bond); 29.46 (t, 1C, CH$_2$ α C$_8$F$_{17}$); 28.3 (s, 1C, CHαCH$_3$); 22.03 (s, 2 C, CH$_3$);

NMR ($^1$H, 80 MHz, CD$_3$COCD$_3$) ppm: 6–5.58 (sex, 1H, CH$_\beta$C$_8$F$_{17}$); 5.56–5.31 (sex, 1H, CH$_\gamma$C$_8$F$_{17}$); 3.31–2.75 (sex, 2H, CH$_2$α C$_8$F$_{17}$) 2.2–2 (sex, 2H, CH$_2$ in β double bond); 1.95–1.61 (m, 1H, CHαCH$_3$); 0.96–0.88 (6H, m, (CH$_3$)$_2$)

IR spectrum of $C_8F_{17}$—$CH_2$—$CH$=$CH$—$CH_2$—$CH$—$(CH_3)_2$ θH—C=3030 cm$^{-1}$; θ CH aliph 2870 cm$^{-1}$, 2930 cm$^{-1}$; 2960 cm$^{-1}$. θ C=C 1660 cm$^{-1}$.

Example 3
Application of Compound

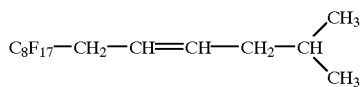

To the Surgery of the Retina

An experimental research of the compound as a temporary substitute of the vitrous humor was conducted in order to determine the tolerance of the retina.

A vitrectomy of the ocular globes is carried out as completely as possible on the rabbit under general anaesthesy, and the compound to be tested is injected (in replacement of the vitrous humor).

Two contact periods with the product are tested: 3 hours and 7 days.

For the 7 days group, an ophthalmological clinical test is conducted at D+4, whereby a quiet anterior segment and a normal eye bottom are observed in all cases.

When the test period is elapsed, the ocular globes are taken and fixed for the purposes of a histological research.

No change is evidenced in the retina; the photoreceptors are preserved and both the internal and external nuclear layers remain well organised.

The conclusion is a good intraocular tolerance of the synthesized hydrogenated fluorinated compound.

Example 4
Preparation of a Solution of the Branched Fluorinated Compound in a Silicone Oil 23 g of the previously prepared compound

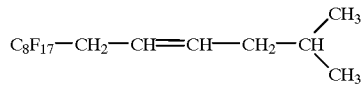

are solubilized in 130 g of polydimethylsiloxane.

The solution is stirred and lightly heated to promote solubilization.

A clear viscous solution with 15 wt. % of the fluorinated compound is obtained with the following characteristics:

transparent liquid aspect,
refractive index: 1.398.
viscosity: $8.10^{-4}$ m$^2$/s (or 800 cSt),
density: 1.04.

Example 5
Synthesis and Characterization of the Compound of the Formula:

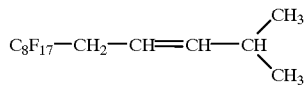

Step 1: synthesis of the fluorinated phosphonium salt 0.5 mole of triphenylphosphine (C$_6$H$_5$)$_3$P and 0.5 mole of fluoroalkyle iodide I CH$_2$ CH$_2$ C$_8$F$_{17}$ are reacted at 95° C. in a reactor in the absence of a solvent.

The product is washed with toluene, then with ether, and dried under vacuum (10$^3$ Pa) during 12 hours.

The yield of the phosphonium salt is 95%.

Step 2

0.025 mole of phosphonium salt, 0.02 mole of isobutyraldehyde (CH$_3$)$_2$—CH—CHO, 1.7 10$^{-2}$ mole of formamide, 0.03 mole of K$_2$CO$_3$ and 25 ml of diaxane are reacted in a reactor, under stirring and dixane reflux during 5 hours.

After removal of the K$_2$CO$_3$, precipitation of the triphenylphosphine oxide, extraction, filtration and "flash" distillation, a final colorless product having the following characteristics is obtained with a yield of 60%:

Aspect: Transparent liquid
Molecular weight: 502
Density: 1.5
Refractive index: 1.34
Viscosity: $<5.10^{-6}$ M$^2$/s (or 5 cSt)

Surface tension: 18 mN/m (at 37° C.)

NMR spectrum

NMR ($^{13}$C, 50 MHz, CDCl$_3$) ppm: 144.20 (s, 1C, CH$_\gamma$C$_8$F$_{17}$); 122.65–111.20 (m, 8 C, C$_8$F$_{17}$); 112.75 (t, 1C, CH$_\beta$C$_8$F$_{17}$); 29.35 (t, 1C, CH$_2\alpha$C$_8$F$_{17}$); 26.71 (s, 1C, CH$_2\alpha$CH$_3$); 22.07 (s, 2 C, (CH$_3$)$_2$);

NMR ($^1$H, 80 MHz, CD$_3$COCD$_3$) ppm: 5.95–5.72 (sex, 1H, CH$_\beta$C$_8$F$_{17}$); 5.55–5.29 (sex, 1H, CH$_\gamma$C$_8$F$_{17}$); 3.5–2.9 (sex, 2H, CH$_2\alpha$C$_8$F$_{17}$); 3–2.5 (m, 1H, CH$\alpha$CH$_3$); 1.16–1.08 (d, 6H, CH$_3$).

We claim:

1. The branched fluorinated compound with the following molecular structure:

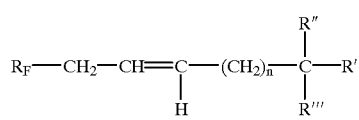

(2)

where R$_F$ is a perfluorinated chain having the formula C$_p$F$_{2p+1}$ with $2 \leq p \leq 12$, and the groups R', R" and R'", identical or not, have each the following formula: (CH$_2$)$_m$—C$_x$H$_y$, with:

n≧0 m≧0 y=2x+1 with x≧0 at least two of the groups R', R" and R'" not being hydrogen atoms, the total number of carbon atoms of the groups R', R" and R'" being lower than 25−n.

2. The branched fluorinated compound according to claim 1, wherein the C$_x$H$_y$ group consists of one or more methyl, ethyl or propyl groups.

3. The branched fluorinated compound according to claim 2, having the following molecular structure:

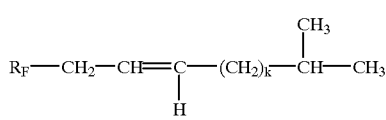

(3)

where k=1, 2, or 3.

4. The branched fluorinated compound according to claim 1, having the following molecular structure:

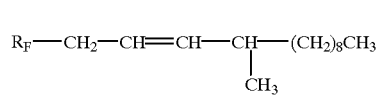

(4)

5. The branched fluorinated compound according to claim 1, having a density in the range between 1.1 and 2.2, said density being an increasing function of p.

6. The branched fluorinated compound according to claim 1, having a refractive index in the range between 1.2 and 1.7, said refractive index being an increasing function of p and the number of carbon atoms in R$_{1H}$ and R$_{2H}$.

7. The branched fluorinated compound according to claim 3, with a solubility in silicone oil greater than 10 wt %, said solubility being an increasing function of k and a decreasing function of p.

8. The branched fluorinated compound according to claim 1, wherein the fluorinated chain R$_F$ is C$_8$F$_{17}$.

9. The branched fluorinated compound according to claim 8, having the formula:

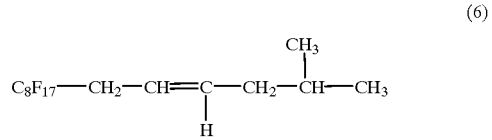

(6)

and having a density of essentially 1.5 and a refractive index of essentially 1.338.

10. A solution or suspension of the branched fluorinated compound according to claim 1 in a silicone or fluorosilicone oil.

11. An artificial composition to replace the vitreous or aqueous humor in the eye, in order to provide an internal buffer effect in the eye, comprising a solution or suspension according to claim 10, in admixture with a pharmaceutically acceptable excipient.

12. The method for preparing a branched fluorinated compound having the following molecular structure:

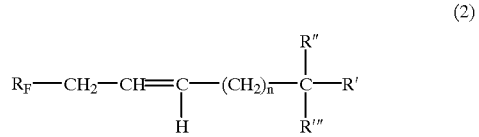

(2)

where R$_F$ is a perfluorinated chain having the formula C$_p$F$_{2p+1}$ with $2 \leq p \leq 12$, and the groups R', R" and R'", identical or not, have each the following formula: (CH$_2$)$_m$—C$_x$H$_y$, with:

n≧0 m≧0 y=2x+1 with x≧0 at least two of the groups R', R" and R'" not being hydrogen atoms, the total number of carbon atoms of the groups R', R" and R'" being lower than 25−n, wherein said phosphonium salt is reacted under heating with a branched aldehyde of the following formula:

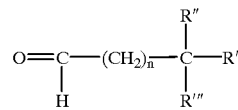

13. The preparation method according to claim 12, wherein:

the triphenylphosphine (C$_6$H$_5$)$_3$P is reacted with a fluoroalkyl iodide, the resultant phosphonium salt is reacted with the following branched aldehyde:

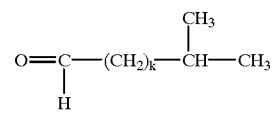

where k=1, 2, or 3, in a solvent, in the presence of potassium carbonate and water acting as a catalyst, the reaction temperature being adjusted to the reflux temperature of the solvent, the potassium carbonate is removed by filtration, the resultant triphenylphosphine oxide is caused to precipitate, after filtration, the branched fluorinated compound is collected by means of distillation steps.

14. The method according to claim 13, for obtaining a colorless liquid purified fluorinated compound, wherein during final steps, a combined extraction in organic and aqueous phases, adapted for eliminating the remaining traces of the solvent and triphenylphosphine oxide is conducted, the aqueous phase is removed by means of decantation, the organic phase is evaporated, a flash distillation under vacuum and cooling of the resultant product with nitrogen are carried out, and the resultant product is subjected to filtration and neutralization steps in order to remove the last residues.

15. An artificial composition of vitreous or aqueous humor for an eye, comprising a branched fluorinated compound according to claim 2, in admixture with a pharmaceutically acceptable excipient.

16. An artificial composition for the temporary replacement of the vitreous or aqueous humor in the eye to promote re-adhesion of the retina, comprising the branched fluorinated compound:

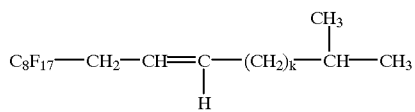

(7)

where k=1, 2, or 3.

* * * * *